United States Patent [19]

Zinreich

[11] Patent Number: 5,743,899

[45] Date of Patent: Apr. 28, 1998

[54] METHOD AND APPARATUS FOR MARKING SKIN WITH INK

[75] Inventor: Eva S. Zinreich, Owings Mills, Md.

[73] Assignee: IZI Medical Products, Owing Mills, Md.

[21] Appl. No.: 764,325

[22] Filed: Mar. 4, 1997

[51] Int. Cl.$^6$ .................................... A61B 17/00
[52] U.S. Cl. .................. 606/1; 606/116; 428/40.2; 428/41.2
[58] Field of Search .................. 606/11, 6; 428/40.2, 428/41.2, 41.6, 42.1; 156/257, 267, 268, 250; D5/63

[56] References Cited

U.S. PATENT DOCUMENTS

| | | |
|---|---|---|
| 2,293,324 | 8/1942 | Vladeff . |
| 3,812,842 | 5/1974 | Rodriquez .................. 128/2 A |
| 3,836,776 | 9/1974 | Gullekson .................. 250/312 |
| 3,867,634 | 2/1975 | Hounsfield .................. 250/360 |
| 4,005,527 | 2/1977 | Wilson et al. .................. 33/111 |
| 4,319,136 | 3/1982 | Jinkins .................. 250/456 |
| 4,505,676 | 3/1985 | Duska .................. 128/653 |
| 4,583,538 | 4/1986 | Onik et al. .................. 128/303 B |
| 4,594,276 | 6/1986 | Relyea .................. 428/40 |
| 4,680,210 | 7/1987 | Corcoran .................. 428/42 |
| 4,838,265 | 6/1989 | Cosman et al. .................. 128/303 B |
| 4,860,331 | 8/1989 | Williams et al. .................. 378/163 |
| 4,918,715 | 4/1990 | Krupnick et al. .................. 378/164 |
| 5,306,271 | 4/1994 | Zinreich et al. .................. 606/1 |
| 5,346,738 | 9/1994 | Samonides .................. 428/40 |
| 5,407,440 | 4/1995 | Zinreich et al. .................. 606/1 |
| 5,469,847 | 11/1995 | Zinreich et al. .................. 128/653.1 |
| 5,578,353 | 11/1996 | Drew, III .................. 428/43 |

FOREIGN PATENT DOCUMENTS

| | | |
|---|---|---|
| 205217 | 1/1968 | U.S.S.R. . |
| 685278 | 9/1979 | U.S.S.R. . |

*Primary Examiner*—Michael Buiz
*Assistant Examiner*—David O. Reip
*Attorney, Agent, or Firm*—Oldham & Oldham Co., LPA

[57] ABSTRACT

A radiation therapy skin marking device which may be used to delineate a radiation therapy portal area on a patient's skin surface. The device includes a set of radiation therapy skin markers which are releasably attached to a backing liner and include an adhesive surface such that the markers may be releasably attached to a patient's skin surface. The markers include ink-printed lines on the adhesive surface so as to facilitate radiation therapy treatments by more obviously defining a radiation therapy portal area. Ink is transferred onto the skin surface from the adhesive surface by depositing it onto the skin or by absorption into the skin so that the marking lines are delineated on the skin surface when the markers are detached. The markers include various shapes including, for example, a marker of substantially circular shape with a ninety degree wedge cut therefrom such that the marker may be used to outline a ninety degree corner and a marker of substantially circular shape with a circular cut-out center such that the marker is defined by a circular outer edge and a circular inner edge both of which circular edges share a common center point.

18 Claims, 3 Drawing Sheets

METHOD AND APPARATUS FOR MARKING SKIN WITH INK

TECHNICAL FIELD

The present invention relates to improvements in devices used to delineate radiation therapy portal areas of patients to be treated with radiation. More specifically, it relates to delineating such areas by applying marking devices of various shapes onto the patient's skin. The markers contain ink lines defining the desired therapy areas which are deposited onto the patient's skin surface so that the lines are observable in the event the markers become detached.

BACKGROUND OF THE INVENTION

In recent years the incidences of cancer in general has significantly increased. Concurrently the use of radiation therapy to treat cancer has increased. Radiation therapy is used to treat cancer patients in two ways: for curative purposes and for palliative reasons.

Virtually all radiation therapy centers are equipped with simulators—a fluoroscopic imaging unit equipped with all the characteristics and parameters found on the radiation treatment units. With the help of diagnostic imaging such as computerized x-ray tomography (CT) and magnetic resonance imaging (MRI), when combined with the fluoroscopic capability of the simulator, a radiation therapy portal (the area through which the treating radiation will be focussed) may be designed. Conventionally, the perimeter, isocenter, and set-up points of this radiation therapy portal are marked on the patients skin with magic markers, fuchsia color, and/or tattoo markings. However, there are many problems with these conventional markers.

The present inventor is a named inventor on two prior patents relating to this field of art. In U.S. Pat. No. 5,306,271, issued Apr. 26, 1994 and U.S. Pat. No. 5,407,440, which is a continuation of the inventors' '271 patent, issued Apr. 18, 1995, a radiation therapy skin marker is taught which is applied to the patient's skin without the problems associated with conventional markers. The marking device comprises adhesive-coated tape-like structures in various shapes which are used to denote the perimeter, isocenter(s) and set-up points of radiation treatment portals on the skin of patients undergoing radiation therapy. The device may be reliably retained in its original position for up to seven days, may be repositioned easily without risk to patient or personnel and is removable without leaving any permanent traces on the patient's skin.

The prior art skin marking device is safe and effective, however, practical experience has taught the inventor that limitations arise when the device is intentionally removed or becomes otherwise detached from the patient's skin. Although the prior art device can be retained adhesively for up to seven days, commonly it is removed or detached from the patient's skin during the course of treatment, or between treatments, resulting in loss of the portal field markings and requiring repositioning and remarking.

SUMMARY OF THE INVENTION

It is an object of the present invention to improve upon devices used to delineate radiation therapy portal areas of patients to be treated with radiation by providing a novel device which deposits marking lines from a marker releasably applied to the patient's skin. The device presented allows for the portal line markings to remain on the patient's skin after the adhesive pieces have been detached or removed.

The object is achieved by a device comprising flat, adhesive-coated tape-like structures in various shapes which are used to denote the perimeter, isocenter(s), and set-up points of radiation treatment portals on the skin of patients undergoing radiation therapy. The device includes pieces shaped such that they may be used to delineate the corners, the edges connecting the corners, the isocenter point(s), and any set-up points of the proposed radiation field. The pieces of the device are adhesively arranged on a backing liner such that they may be removed individually or in preconfigured groups. The ink lines comprising the portal field markings may be disposed on both the adhesive surface and the top surface. Alternatively, the ink lines may be disposed solely on the surface of the marker containing the adhesive; this alternative requires that the marker material be sufficiently transparent to allow the lines to remain observable through the marker while it is attached to the patient's skin. The markers are pealably released from the backing liner and the adhesive surface is attached to the patient's skin thereby delineating the desired portal markings either disposed on both surfaces or solely on the bottom adhesive surface and showing through the marker. The ink lines disposed on the adhesive surface of the marker are at least partially transferred to and received by the patient's skin so that the line markings continue to delineate the portal field even when the markers become detached, whether intentionally or accidentally.

The ink deposited onto the patient's skin is substantially permanent or indelible while remaining non-toxic. The ink should be resistant to removal by mere bathing so that the deposited ink markings may remain observable for at least several days; should the need arise to reposition or otherwise eliminate the markings, the ink must preferably be removable by vigorous scrubbing with strong cleansing agents or soap solutions. The ink distribution at the backing liner-adhesive coating interface must remain substantially with the adhesive coating; this can be accomplished by coating the backing liner with an appropriate silicon or fluorine-based release coating. Once the marker is applied to the patient's skin, the ink initially deposited onto the adhesive coating on the surface of the marker must be substantially transferred by absorption into the patient's skin. It is therefore necessary for the ink to have a finite affinity for the patient's skin so that the transfer of ink at the skin-marker interface may be achieved. Upon application of the marker to the skin, a substantial amount of ink will initially remain with the adhesive coating for which it has a greater affinity. As the ink is absorbed into the first layer of skin an equilibrium distribution of ink will be established at the skin-adhesive coating interface. As subsequent layers of skin absorb the ink, the equilibrium distribution will shift in the direction favoring absorption of ink into the skin. Over time a substantial amount of ink will be transferred from the adhesive coating into the patient's skin.

3

Figure 2:
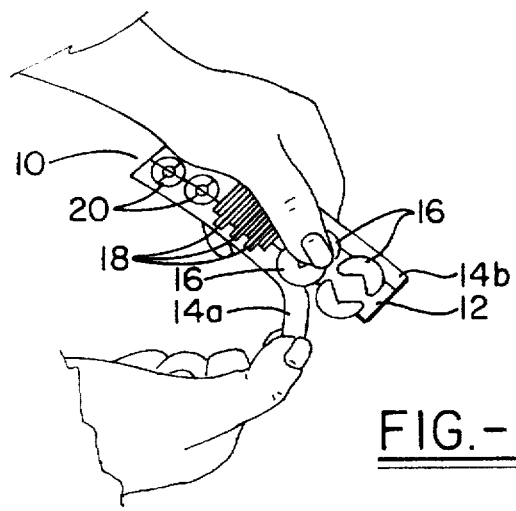

FIG. 2 shows a perspective view of the preferred embodiment of the present invention as a strip part of the backing liner is being removed.

Figure 1A:
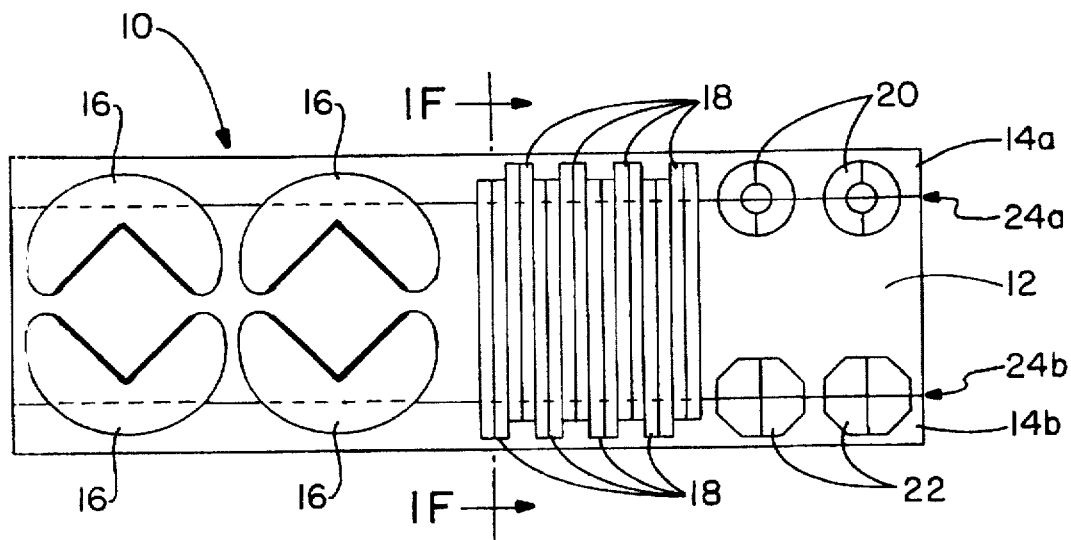
FIG. 1A shows a plan view of a preferred embodiment of a set of radiation therapy skin markers of the present invention.
Figure 2A:
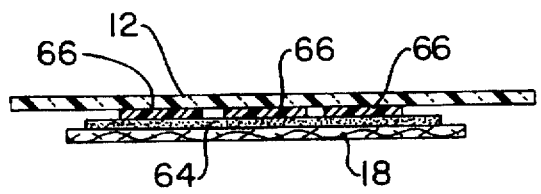

FIG. 2A shows a cross-section view of the preferred embodiment of the backing liner-adhesive coating-skin surface interface taken from line 1F—1F in FIG. 1A.

Figure 3B:
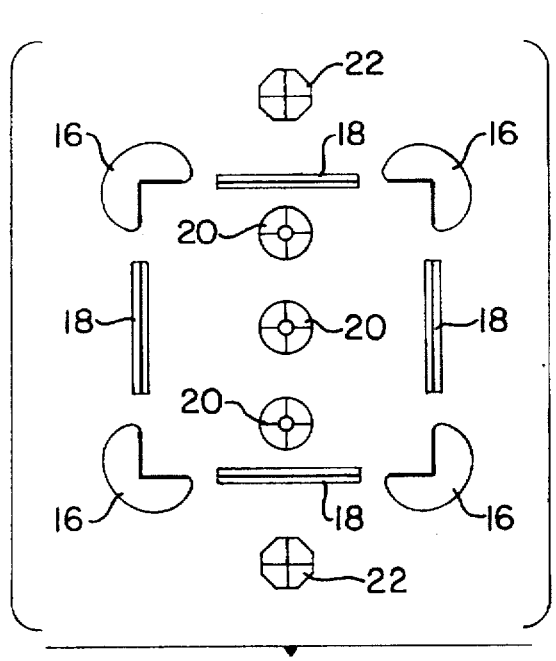
Figure 3A:
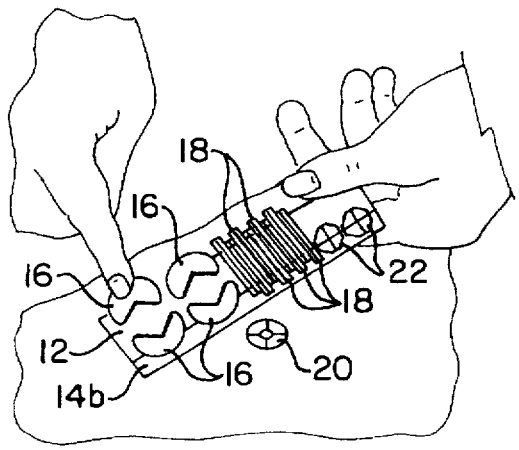

FIG. 3A shows a perspective view of the preferred embodiment of the present invention as the markers are used after a strip part of the backing liner has been removed.

FIG. 3B shows a perspective view of the markers of the present invention after the markers have been applied.

Figure 4A:
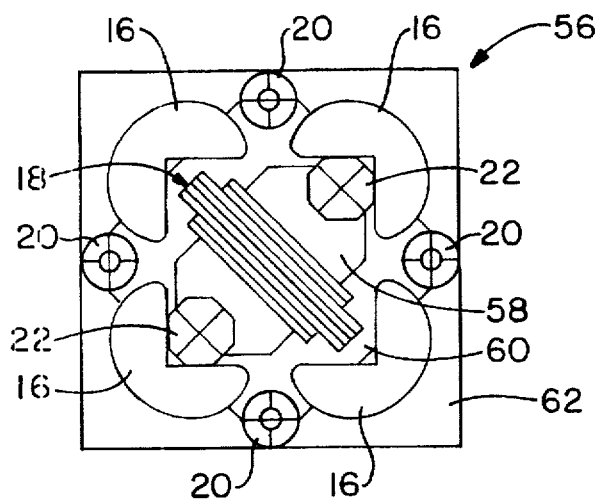

FIG. 4A shows a plan view of a second embodiment of a set of radiation therapy skin markers.

Figure 4B:
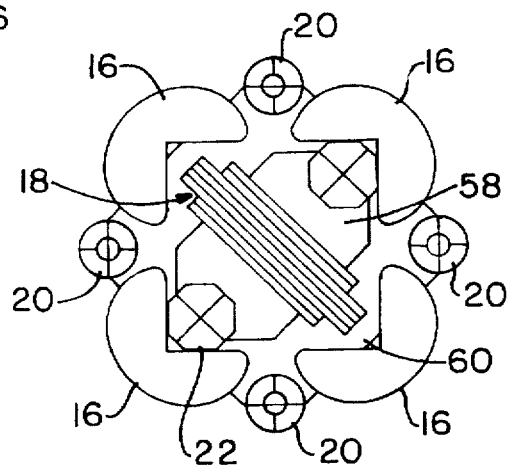

FIG. 4B shows a plan view of a second embodiment of a set of radiation therapy skin markers after a backing card is removed.

Figure 4C:
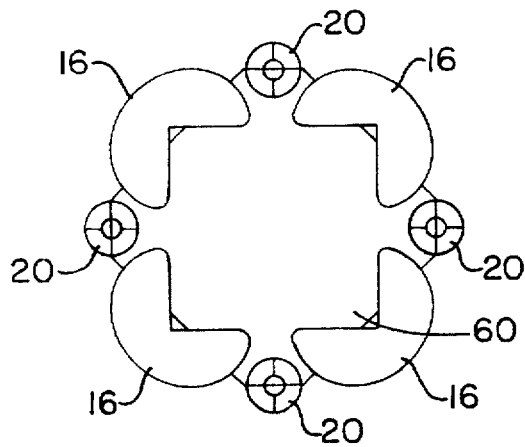

FIG. 4C shows a plan view of a bottom set of markers from the second embodiment of a set of radiation therapy skin markers.

Figure 4D:
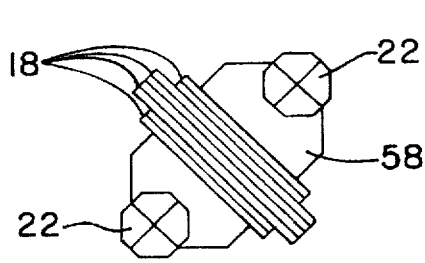

FIG. 4D shows a plan view of a top set of markers from the second embodiment of a set of radiation therapy skin markers.

Figure 5:
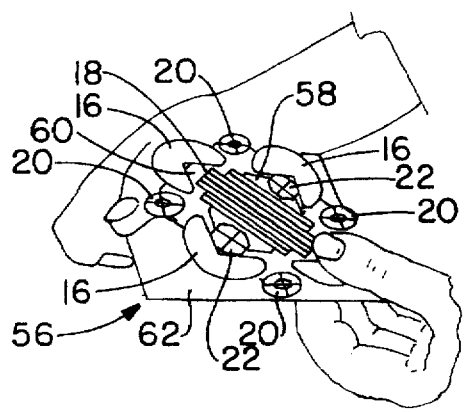

FIG. 5 shows a perspective view of the second embodiment of a set of radiation therapy skin markers as the backing card is removed.

Figure 6:
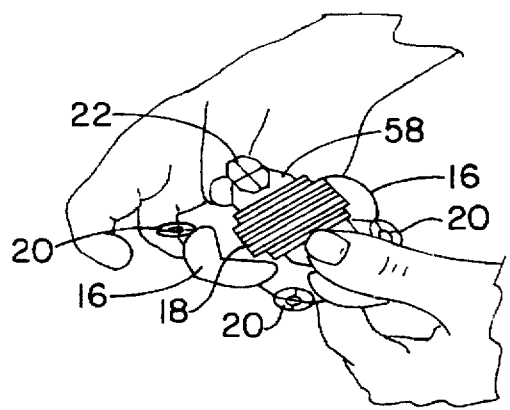

FIG. 6 shows a perspective view of the second embodiment of a set of radiation therapy skin markers as the bottom set of markers and the top set of markers are being separated from each other after the backing card has been removed.

Figure 7:
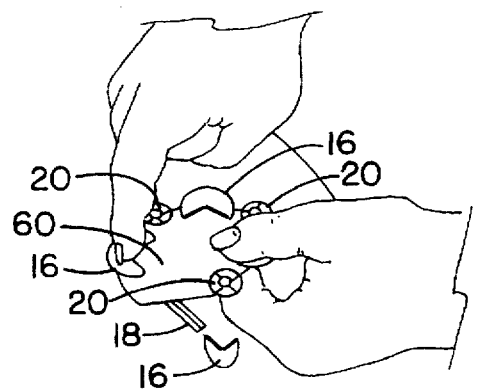

FIG. 7 shows a perspective view of a bottom set of markers from a second embodiment of a set of radiation therapy skin markers as the markers are being applied.

DESCRIPTION OF THE PREFERRED EMBODIMENT

Turning to the drawings, FIG. 1A shows a plan view of a preferred embodiment of the present invention in the form of a set of radiation therapy skin markers 10. The set of skin markers 10 in this embodiment has various markers (described below), a backing liner 12, and two backing strips 14a and 14b.

Figures 1B, 1C, 1F:
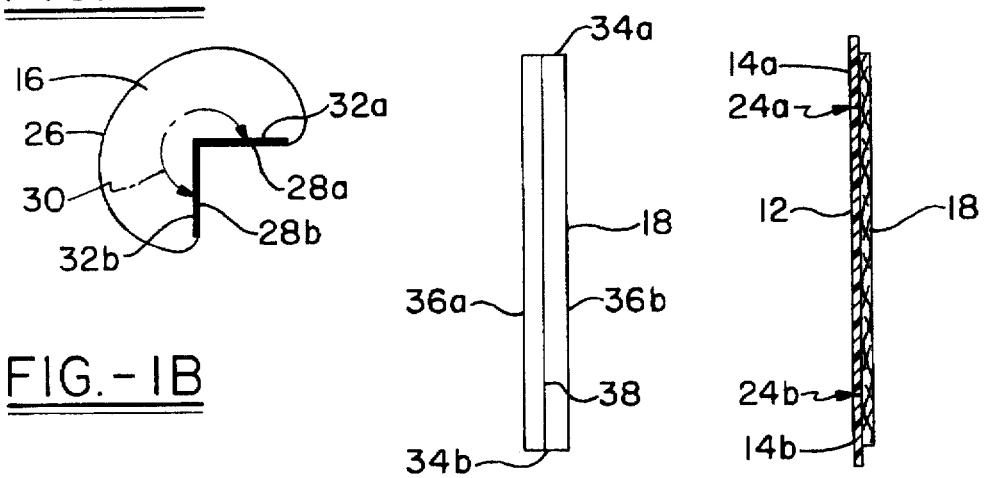
FIG. 1B shows a corner marker of the present invention.
FIG. 1C shows a line marker of the present invention.
FIG. 1F shows a cross-section view of a preferred embodiment of a set of radiation therapy skin markers of the present invention taken from line 1F—1F in FIG. 1A.
Figure 1D:
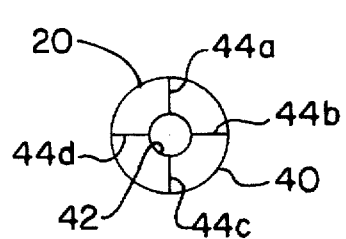
FIG. 1D shows a isocenter marker of the present invention.
Figure 1E:
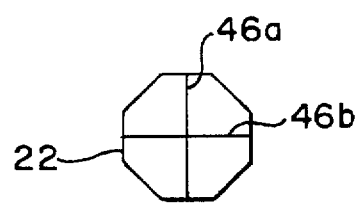
FIG. 1E shows a set-up point marker of the present invention.

In their most preferred embodiment, the markers comprise corner markers 16 (see also FIG. 1B), line markers 18 (see also FIG. 1C), isocenter markers 20 (see also FIG. 1D), and set-up point markers 22 (see also FIG. 1E). These markers are mounted on a backing liner 12 as shown in FIGS. 1A and 1F. As described below, the corner markers 16 and the line markers 18 can be used, respectively, to mark the corners and edges of a square or rectangle radiation therapy portal (as shown in FIG. 3B). The isocenter markers 20 and the set-up point markers 22 can be used, respectively, to mark any isocenters and set-up points necessary to a particular radiation therapy treatment (as shown in FIG. 3B). The markers 16, 18, 20, and 22 have a top surface (shown in FIG. 1A) and a bottom surface (not shown). In their most preferred embodiment, the markers 16, 18, 20, and 22 are made from a conventional breathable material, preferably printable spunbonded nylon available from FLEXcon Company, Inc. as item number PBN-1000-W. However, any substrate material which is capable of receiving an adhesive layer disposed on one side could be used to accomplish the purposes of this invention. In addition, the markers 16, 18, 20, and 22 have adhesive, preferably skin contact adhesive available from FLEXcon Company, Inc. as item number H-566, applied to their entire bottom surface in a conventional manner. The 3M Company has material available which could be substituted for these preferred materials.

As shown in FIG. 1B, a preferred corner marker 16 is defined by an arcuate edge 26 and two straight edges 28a and 28b. The straight edges 28a and 28b are perpendicular to each other thereby forming a two hundred seventy degree angle 30. The corner markers 16 are placed by a radiation therapist (described in more detail later) such that the two hundred seventy degree angle 30 of each corner marker 16 will outline a ninety degree angle of a corner of a specified square or rectangular radiation therapy portal (as shown in FIGS. 3A and 3B). In addition, the straight edges 28a and 28b include printing 32a and 32b to help create a discernable target for a radiation therapist performing radiation therapy treatments.

As shown in FIG. 1C, a preferred line marker 18 is somewhat rectangular in shape and defined by short edges 34a and 34b and long edges 36a and 36b. The long edges 36a and 36b are multiple times the length of the short edges 34a and 34b. Each line marker 18 includes a printed line 38 extending between the short edges 34a and 34b and parallel to the long edges 36a and 36b. The line markers 18 are placed by a radiation therapist (described in more detail later) such that the printed lines 38 of each line marker 16 outline the edges of a specified square or rectangular radiation therapy portal (as shown in FIGS. 3A and 3B). The printed lines 38 help create a discernable target for a radiation therapist performing radiation therapy treatments.

As shown in FIG. 1D, a preferred isocenter marker 20 is circularly shaped with a circular cut-out center and is defined by a circular outer edge 40 and circular inner edge 42. Each isocenter marker 20 includes four printed lines 44a–44d extending radially from the circular inner edge 42 to the circular outer edge 40. The printed lines 44a–44d are further defined by the fact that if they were extended beyond the circular inner edge 42, they would intersect at a point which defines a common center of circles defined by the circular outer edge 40 and the circular inner edge 42 and would intersect in such a way that lines 44a and 44c would each be perpendicular to lines 44b and 44d. The isocenter markers 20 are placed by a radiation therapist (described in more detail later) such that the printed lines 44a–44d define an isocenter of a specific radiation therapy portal as the point where the lines 44a–44d would intersect thereby assisting a radiation therapist perform radiation therapy treatments (see FIGS. 3A and 3B).

As shown in FIG. 1E, a preferred set-up point marker 22 is octagonally shaped and includes two printed lines 46a and 46b. The printed lines 46a and 46b are positioned such that they perpendicularly bisect each other. The set-up point markers 22 are placed by a radiation therapist (described in more detail later) such that the intersection of the printed lines 46a and 46b define a set-up point of a specific radiation therapy portal thereby assisting a radiation therapist perform radiation therapy treatments (see FIGS. 3A and 3B).

As shown in FIG. 1A, the backing liner 12 includes two die cuts 24a and 24b along its full length which define backing strips 14a and 14b. The die cuts 24a and 24b are designed in a way to facilitate the removal of backing strips 14a and 14b without disturbing the various markers 16, 18, 20, and 22 on the backing liner 12. FIG. 2 shows a perspective view of the present invention as a backing strip 14a is being removed. FIG. 3A shows a perspective view of the present invention after the removal of backing strip 14a.

As shown in FIGS. 2, and 3A, but irrespective of the shape or pattern of a particular marker, except for purposes of illustration, once the backing strip 14a has been removed, bottom surfaces of portions of the corner markers 16, the line markers 18, and the isocenter markers 20 are exposed. As described above, and depicted in FIG. 2A, the entire bottom surface of the markers 16, 18, 20, and 22 includes a pressure sensitive adhesive coating 64 into which is deposited an ink layer 66 in defined patterns. Backing liner 12 is coated with an appropriate, preferably silicon-based, ink-resistant release material to prevent the ink from being retained on the backing liner when the marker is released. Thus, when the bottom surfaces are exposed, the adhesive coating 64 is exposed which enables a radiation therapist to apply the markers onto the patient as shown in FIG. 3A. The ink line markings 66, placed into the adhesive coating 64, thereby come in contact with the patient's skin when the markers are positioned and attached. This allows line markings 66 to be impressibly deposited from the adhesive surface of marker 18 and received by the patient's skin. In its most preferred embodiment, the composition of the ink will be such that the patient's skin has a finite affinity for the ink thereby allowing an equilibrium to be established at the skin-adhesive coating interface. Transfer of ink into the patient's skin is achieved by the driving of the equilibrium in the direction favoring absorption into the skin effected by successive absorption into subsurface skin layers. Thus, with reference to FIG. 2A, the ink line markings 66 are disposed into the adhesive coating 64 on the bottom surface of marker 18, the surface by which line marker 18 is releasably mounted onto backing liner 12. It is preferred but not required that the substrate material from which each marker is made be substantially transparent so that ink deposited into or on adhesive coating 64 can be seen through the adhesive and the marker 16 once the marker is applied to the patient's skin. Alternatively, if a substrate material is selected which is not sufficiently transparent to achieve this objective, then it is again preferred but not required that the line markings 66 be recreated, identically and in the same position, on the top surface of each marker.

FIGS. 4A, 4B, 4C, 4D, 5, 6, and 7 show views of a second embodiment of a set of radiation therapy skin markers 56. As shown in FIG. 4A, the configurations of the various markers 16, 18, 20, and 22, are as described above. The main difference between this second embodiment 56 and the preferred embodiment 10 is that the markers 16, 18, 20, and 22 are organized differently such that they are arranged on a top backing liner 58, a bottom backing liner 60, and a backing card 62. This arrangement allows exposure of portions of the corner markers 16 and the isocenter markers 20 after the backing card 62 is removed (as shown in FIGS. 4A, 4B, and 5). In addition, the arrangement allows exposure of portions of the line markers 18 and the set-up point markers 22 when the top backing liner 58 and the bottom backing liner 60 are separated (as shown in FIGS. 4D and 6). The markers 16, 18, 20, and 22 are all applied as described above (as shown in FIG. 7).

Although particular and preferred embodiments of the above-described method and apparatus for marking skin with ink have been shown and described herein, it is to be understood that they can be modified without departing from the scope of the present invention, and all such modifications and equivalents are intended to be covered.

What is claimed is:

1. A device for marking skin surfaces comprising:

a substrate having a first and second surface;

an adhesive layer disposed on said second surface;

a first ink layer disposed on said adhesive layer, said first ink layer defining a pattern which is transferable onto said skin surface when placed in contact with said skin surface; and a backing liner removably covering said adhesive layer and said first ink layer;

whereby said pattern may be subsequently and selectively removed from said skin surface.

2. The device of claim 1 wherein a second ink layer defining said pattern is further disposed on said first surface of said substrate.

3. The device of claim 1 wherein said substrate is made of fibrous, breathable material.

4. The device of claim 3 wherein said fibrous, breathable material is printable spun-bonded nylon.

5. The device of claim 1 wherein said substrate is substantially transparent so that said ink layer defining said pattern is observable while said substrate is in contact with a patient's skin.

6. The device of claim 1 wherein said substrate is of substantially circular shape with a circular cut-out center such that the substrate is defined by a circular outer edge and a circular inner edge both of which circular edges share a common center point such that said pattern defined by said ink layer is comprised of lines extending from the inner edge to the outer edge along imaginary lines extending radially from the common center point to the circular outer edge.

7. The device of claim 6 wherein said wedge cut from said substrate is a ninety degree wedge so that the corner boundary delineated by said pattern is a ninety degree corner boundary.

8. The device of claim 1 wherein said substrate is of substantially circular shape with a wedge cut therefrom so that the substrate may be used to delineate a corner boundary such that said pattern defined by said ink layer is comprised of lines on edges outlining the corner boundary.

9. The device of claim 1 wherein said substrate is of substantially rectangular shape wherein the length of the rectangle is several times the width of the rectangle such that said pattern defined by said ink layer is comprised of a straight line.

10. The device of claim 9 wherein said angle is ninety degrees so that the lines comprising said pattern are perpendicular to one another so as to define at least one ninety degree angle.

11. The device of claim 1 wherein said pattern defined by said ink layer is comprised of two straight lines crossing at an angle.

12. The device of claim 1 wherein said backing liner comprises a surface onto which the substrate or a set of substrates is removably adhered, said backing liner including a die cut such that a portion of the liner which is adhered to a portion of at least one substrate of the set may be removed without disturbing the set of substrates from a remaining portion of the backing liner and thereby exposing at least a portion of the substrate surface including adhesive of at least one of the substrates of the set.

13. The device of claim 1 wherein said backing liner includes more than one die cut such that more than one portion of the liner may be removed without disturbing the substrates removably attached to the remaining portion of the backing liner.

14. The device of claim 13 wherein said wedge cut from said corner boundary marker is a ninety degree wedge so that the corner boundary delineated by said pattern is a ninety degree corner boundary.

15. The device of claim 13 wherein said straight lines of said set-up point marker cross at an angle of ninety degrees so that the lines comprising said pattern are perpendicular to one another so as to define at least one ninety degree angle.

16. The device of claim 1 wherein said ink layer is at least partially deposited onto a patient's skin when said substrate is removed.

17. The device of claim 1 further comprising a set of substrates including at least one of a corner boundary marker, a line boundary marker, an isocenter marker, or a set-up point marker configured to be used to define and delineate a radiation therapy portal area;

said corner boundary marker being of substantially circular shape with a wedge cut therefrom so that the substrate may be used to delineate a corner boundary of a radiation therapy portal area such that said pattern defined by said ink layer is comprised of lines on edges outlining the corner boundary;

said line boundary marker being of substantially rectangular shape wherein the length of the rectangle is several times the width of the rectangle so that the substrate may be used to delineate a boundary of a radiation therapy boundary such that said pattern defined by said ink layer is comprised of a straight line;

said isocenter marker being of substantially circular shape with a circular cut-out center such that the substrate is defined by a circular outer edge and a circular inner edge both of which circular edges share a common center point so that the substrate may be used to delineate an isocenter of a radiation therapy portal area such that said pattern defined by said ink layer is comprised of lines extending from the inner edge to the outer edge along imaginary lines extending radially from the common center point to the circular outer edge;

said set-up point marker having said pattern defined by said ink layer comprised of two straight lines crossing at an angle.

18. A method of marking a person's skin with a marker, said marker having a substrate with a first and second surface; an adhesive layer disposed on said second surface; an ink layer disposed on said adhesive layer, said ink layer defining a pattern; and a backing liner removably covering said adhesive layer; said method comprising steps of a) removing said substrate from said backing liner;

b) applying said second surface to the skin of a person such that said pattern defined by said ink layer comes in contact with said skin; and c) allowing said substrate to remain in contact with said skin so that said ink layer defining said pattern may be transferred at least in part to said skin through absorption.

* * * * *